US011577125B2

(12) United States Patent
Onuki

(10) Patent No.: US 11,577,125 B2
(45) Date of Patent: Feb. 14, 2023

(54) SENSOR DEVICE-EQUIPPED GOLF SHOES

(71) Applicant: SUMITOMO RUBBER INDUSTRIES, LTD., Hyogo (JP)

(72) Inventor: Masahide Onuki, Hyogo (JP)

(73) Assignee: SUMITOMO RUBBER INDUSTRIES, LTD., Hyogo (JP)

( * ) Notice: Subject to any disclaimer, the term of this patent is extended or adjusted under 35 U.S.C. 154(b) by 318 days.

(21) Appl. No.: 16/536,367

(22) Filed: Aug. 9, 2019

(65) Prior Publication Data

US 2020/0047026 A1 Feb. 13, 2020

(30) Foreign Application Priority Data

Aug. 10, 2018 (JP) .............................. JP2018-151857

(51) Int. Cl.
*A63B 24/00* (2006.01)
*A63B 71/06* (2006.01)
(Continued)

(52) U.S. Cl.
CPC ...... *A63B 24/0003* (2013.01); *A63B 69/3667* (2013.01); *A63B 71/0622* (2013.01);
(Continued)

(58) Field of Classification Search
CPC ............ A63B 24/0003; A63B 71/0622; A63B 69/3667; A63B 2220/836; A63B 2220/802; A63B 2220/89; A63B 2225/50; A63B 2102/32; A63B 2220/40; A61B 5/6807; A61B 2560/0242; A61B 2562/0223; A61B 5/1122; A61B 5/0024; A61B 5/6895; A61B 2503/10; A61B 2562/0219; A61B 5/1114; G06K 9/00342
See application file for complete search history.

(56) References Cited

U.S. PATENT DOCUMENTS 10,300,333 B2 * 5/2019 Dau .................... G09B 19/0038
2002/0161461 A1 * 10/2002 Lobb .................. A63B 24/0021
700/91
(Continued)

FOREIGN PATENT DOCUMENTS

JP 2013-532568 A 8/2013
JP 2017-074382 4/2017
(Continued)

OTHER PUBLICATIONS

Jul. 19, 2022 Japanese Office Action in corresponding Japanese Patent Application No. 2018-151857 and English translation thereof.

*Primary Examiner* — Jeffrey S Vanderveen
(74) *Attorney, Agent, or Firm* — Greenblum & Bernstein, P.L.C.

(57) ABSTRACT

Provided is a sensor device-equipped golf shoes comprising: golf shoes including a left and right pair of a first shoe and a second shoe to be worn by a golfer; and a sensor device attached to the golf shoes. The sensor device includes one or more sensor modules configured to measure sensor data pertaining to at least one of an orientation of the first shoe when the golfer takes a shot, an orientation of the second shoe when the golfer takes a shot, and a positional relationship between the first shoe and the second shoe when the golfer takes a shot.

23 Claims, 13 Drawing Sheets

(51) Int. Cl.
    *A63B 69/36*     (2006.01)
    *A61B 5/00*     (2006.01)
    *A63B 102/32*     (2015.01)

(52) U.S. Cl.
    CPC ......... *A61B 5/6807* (2013.01); *A63B 2102/32* (2015.10); *A63B 2220/40* (2013.01); *A63B 2220/802* (2013.01); *A63B 2220/836* (2013.01); *A63B 2220/89* (2013.01); *A63B 2225/50* (2013.01)

(56) References Cited

U.S. PATENT DOCUMENTS

| | | |
|---|---|---|
| 2007/0243942 A1 | 10/2007 | Elliott |
| 2010/0184563 A1 | 7/2010 | Molyneux |
| 2011/0230274 A1 | 9/2011 | Lafortune et al. |
| 2012/0035003 A1 | 2/2012 | Moran et al. |
| 2013/0041617 A1 | 2/2013 | Pease et al. |
| 2015/0358770 A1* | 12/2015 | Somiya ................. H04W 4/029 340/539.13 |
| 2016/0338644 A1* | 11/2016 | Connor ................. A61B 5/1126 |
| 2017/0239551 A1 | 8/2017 | Pease et al. |
| 2019/0108391 A1 | 4/2019 | Matsuzawa |

FOREIGN PATENT DOCUMENTS

| | | |
|---|---|---|
| JP | 2017-200589 | 11/2017 |
| JP | 2017-205213 | 11/2017 |
| JP | 2018-008068 | 1/2018 |
| KR | 10-2012-0119624 | 10/2012 |
| KR | 10-1672481 | 11/2016 |
| KR | 10-1736489 | 5/2017 |

* cited by examiner

Fig.9A

GOLFER NAME  (ID: abc123456)

MONDAY, JULY 23, 2018
ABC GOLF COURSE

THE RECORDS FOR EACH OF YOUR SHOTS ARE SHOWN BELOW.

| HOLE | SHOT | CLUB USED | DISTANCE | LIE (FWD-BWD) | | LIE (RIGHT-LEFT) | | STANCE | SCORE | |
|---|---|---|---|---|---|---|---|---|---|---|
| 1 | FIRST | DRIVER | 235yard | TOE-DOWN | 2° | LEFT FOOT UP | 1° | S50°W | PAR4 | 0 |
|  | SECOND | NO. 7 IRON | 148yard | TOE-UP | 5° | RIGHT FOOT UP | 11° | S58°W | | |
|  | THIRD | PUTTER | 7yard | TOE-DOWN | 3° | RIGHT FOOT UP | 1° | *** | | |
|  | FOURTH | PUTTER | 1yard | TOE-UP | 1° | LEFT FOOT UP | 1° | *** | | |
| 2 | FIRST | NO. 6 IRON | 171yard | FLAT | 0° | RIGHT FOOT UP | 2° | S32°W | PAR3 | +1 |
|  | SECOND | SAND WEDGE | 15yard | TOE-DOWN | 2° | RIGHT FOOT UP | 5° | S40°E | | |
|  | THIRD | PUTTER | 5yard | FLAT | 0° | RIGHT FOOT UP | 1° | *** | | |
|  | FOURTH | PUTTER | 1yard | TOE-UP | 1° | LEFT FOOT UP | 2° | *** | | |
| ⋮ | ⋮ | ⋮ | ⋮ | ⋮ | ⋮ | ⋮ | ⋮ | ⋮ | ⋮ | ⋮ |
| 18 | FIRST | *** | *** | *** | *** | *** | *** | *** | *** | *** |
|  | SECOND | *** | *** | *** | *** | *** | *** | *** | *** | *** |
|  | THIRD | *** | *** | *** | *** | *** | *** | *** | *** | *** |
|  | FOURTH | *** | *** | *** | *** | *** | *** | *** | *** | *** |
|  | FIFTH | *** | *** | *** | *** | *** | *** | *** | *** | *** |

SCORE: 85

W1

SENSOR DEVICE-EQUIPPED GOLF SHOES

CROSS REFERENCE TO RELATED APPLICATIONS

This application claims a priority to Japanese Patent Application No. 2018-151857 filed on Aug. 10, 2018, which is hereby incorporated by reference in its entirety.

FIELD OF INVENTION

The present invention relates to sensor device-equipped golf shoes, a sensor device included therein, a golf measurement system including the same, and a golf measurement method and program.

BACKGROUND

Systems that record a golfer's shots during a round on a golf course have been known for some time. For example, according to JP 2013-532568A, various types of data pertaining to shots is collected during a round via a mobile terminal carried by the golfer, and based on that data, information such as the number of shots taken per hole, the distance of each shot, the type of golf club used for each shot, the score in the round, and so on is managed and analyzed.

SUMMARY OF INVENTION

Incidentally, the challenge of golf lies in that while a golfer may be able to make consistently accurate shots at a driving range, he or she may not be able to do the same on an actual golf course. This often stems from the fact that the conditions of the location where the golfer shoots from on an actual course are different from the stalls at a driving range. In other words, at a driving range, golfers shoot from a horizontal mat (ground surface), and can easily know which direction the shot will take by looking at the mat frame, the orientation of the stall, and so on. However, at a golf course, golfers take few shots from a horizontal ground surface, and even the tee grounds are sometimes sloped.

The slope of the ground surface, called the "lie", can be broadly classified into the slope of the forward-backward direction of the golfer's body when taking his or her address (called "toe-up", "toe-down", or the like), and the slope of the left-right direction of the golfer's body (called "left foot up" or "left foot down"), and these are sometimes combined as well. For example, when in a toe-up state, if the ball is addressed in the same manner as when the ground surface is horizontal, the direction of the normal line of the golf club face will be oriented slightly to the left due to the loft angle of the face. Thus if the ball is struck in that state, it will travel to the left, with a slight leftward curve. In other words, a golfer must take the lie into account with every shot. Some golf schools instruct golfers to change how they shoot depending on the lie.

How the golfer stands with respect to the hitting direction when addressing the ball is also very important. Driving ranges have signs that tell golfers which direction to hit, but actual golf courses have no such signs. On a golf course, the surrounding scenery, the state of the lie, and so on affect the golfer's senses, which makes it difficult to stand precisely facing the desired direction. Under such circumstances, the ball will not travel in the desired direction if the position of the golfer's left and right feet (called the "stance") is incorrect when addressing the ball.

In light of the foregoing, simply obtaining data such as the distance of each shot, the score, and so on during a round is insufficient. Effective feedback which helps the golfer improve cannot be given unless the orientation of the feet during each shot, which indicates the lie, the stance, and the like, is known. Conversely, if the orientation of the feet during a shot is known, characteristics such as the golfer having trouble with toe-up shots, or if a pond is in view, unconsciously shifting his or her stance away from the pond, can be discovered. In other words, information necessary for improvement, such as the golfer's habits, issues, and the like, can be made clear.

An object of the present invention is to provide sensor device-equipped golf shoes capable of collecting sensor data for analyzing the orientation of a golfer's feet during a shot, as well as a sensor device included therein, a golf measurement system including the same, and a golf measurement method and program.

Sensor device-equipped golf shoes according to a first aspect include golf shoes having a left and right pair of a first shoe and a second shoe to be worn by a golfer, and a sensor device attached to the golf shoes. The sensor device includes one or more sensor modules that measure sensor data pertaining to at least one of an orientation of the first shoe when the golfer takes a shot, an orientation of the second shoe when the golfer takes a shot, and a positional relationship between the first shoe and the second shoe when the golfer takes a shot.

Sensor device-equipped golf shoes according to a second aspect are the sensor device-equipped golf shoes according to the first aspect, wherein the one or more sensor modules include at least one sensor, as a sensor for measuring at least one of the orientation of the first shoe and the orientation of the second shoe, selected from a group including the following:

(1) an accelerometer attached to at least one of the first shoe and the second shoe (2) a terrestrial magnetism sensor attached to at least one of the first shoe and the second shoe (3) a slope sensor attached to at least one of the first shoe and the second shoe Sensor device-equipped golf shoes according to a third aspect are the sensor device-equipped golf shoes according to the first or second aspects, wherein the one or more sensor modules include at least one sensor, as a sensor for measuring the positional relationship between the first shoe and the second shoe, selected from a group including the following:

(1) an ultrasonic sensor attached to at least one of the first shoe and the second shoe (2) a radar sensor attached to at least one of the first shoe and the second shoe (3) terrestrial magnetism sensors attached to both the first shoe and the second shoe (4) atmospheric pressure sensors attached to both the first shoe and the second shoe (5) accelerometers attached to both the first shoe and the second shoe (6) slope sensors attached to both the first shoe and the second shoe Sensor device-equipped golf shoes according to a fourth aspect are the sensor device-equipped golf shoes according to any one of the first to third aspects, wherein the sensor device further includes: a communication unit connected to an external device wirelessly or over a wire; and a control unit that controls the operations of the one or more sensor modules and the communication unit, and sends measurement data including at least one of the sensor data and processed data obtained by processing the sensor data to the external device through the communication unit.

A sensor device according to a fifth aspect is a sensor device configured to be attached to golf shoes including a left and right pair of a first shoe and a second shoe to be worn by a golfer, the device including: one or more sensor modules that measure sensor data pertaining to at least one of an orientation of the first shoe when the golfer takes a shot, an orientation of the second shoe when the golfer takes a shot, and a positional relationship between the first shoe and the second shoe when the golfer takes a shot; a communication unit connected to an external device wirelessly or over a wire; and a control unit that controls the operations of the one or more sensor modules and the communication unit, and sends measurement data including at least one of the sensor data and processed data obtained by processing the sensor data to the external device through the communication unit.

A golf measurement system according to a sixth aspect includes the sensor device-equipped golf shoes according to the fourth aspect and an analysis device that analyzes a shot taken by the golfer. The control unit sends the measurement data to the analysis device through the communication unit. The analysis device includes: an analysis unit that, on the basis of the measurement data, analyzes the orientation of feet when the golfer takes a shot; and a display unit that displays a result of analyzing the orientation of the feet.

A golf measurement system according to a seventh aspect is the golf measurement system according to the sixth aspect, further including a sensor unit-equipped golf club including a golf club to be used by the golfer and a sensor unit attached to the golf club The sensor unit includes one or more second sensor modules, a second communication unit, and a second control unit. The one or more second sensor modules measure second sensor data indicating a state of the golf club when the golfer takes a shot. The second communication unit is connected to the analysis device wirelessly or over a wire. The second control unit controls the operations of the one or more second sensor modules and the second communication unit, and sends second measurement data including at least one of the second sensor data and second processed data obtained by processing the second sensor data to the analysis device through the second communication unit.

A golf measurement method according to an eighth aspect includes the following. Note that the sensor module-equipped shoes indicated below include golf shoes having a left and right pair of a first shoe and a second shoe, and one or more sensor modules that are attached to the golf shoes and that measure sensor data pertaining to at least one of an orientation of the first shoe, an orientation of the second shoe, and a positional relationship between the first shoe and the second shoe.

(1) a golfer taking a shot while wearing sensor module-equipped shoes
(2) obtaining the sensor data from the one or more sensor modules
(3) analyzing, on the basis of the sensor data, the orientation of feet when the golfer takes a shot A golf measurement program according to a ninth aspect causes a computer to execute the following. Note that the computer is connected to sensor module-equipped shoes. The sensor module-equipped shoes indicated below include golf shoes having a left and right pair of a first shoe and a second shoe, and one or more sensor modules that are attached to the golf shoes and that measure sensor data pertaining to at least one of an orientation of the first shoe, an orientation of the second shoe, and a positional relationship between the first shoe and the second shoe.

(1) obtaining the sensor data from the one or more sensor modules
(2) analyzing, on the basis of the sensor data, the orientation of feet when the golfer takes a shot According to the foregoing aspects, sensor data for analyzing the orientation of a golfer's feet when taking a shot can be collected. The lie, stance, and so on when taking the shot can be understood based on the information of the orientation of the feet during the shot, which makes it possible to obtain information that can help the golfer improve. Alternatively, the information of the orientation of the feet during the shot can also be useful in developing golf-related products such as golf clubs.

DETAILED DESCRIPTION OF THE PREFERRED EMBODIMENTS

Sensor device-equipped golf shoes, a sensor device included therein, a golf measurement system including the same, and a golf measurement method and program according to an embodiment of the present invention will be described hereinafter with reference to the drawings.

1. Overall Configuration of Golf Measurement System

Figure 1:
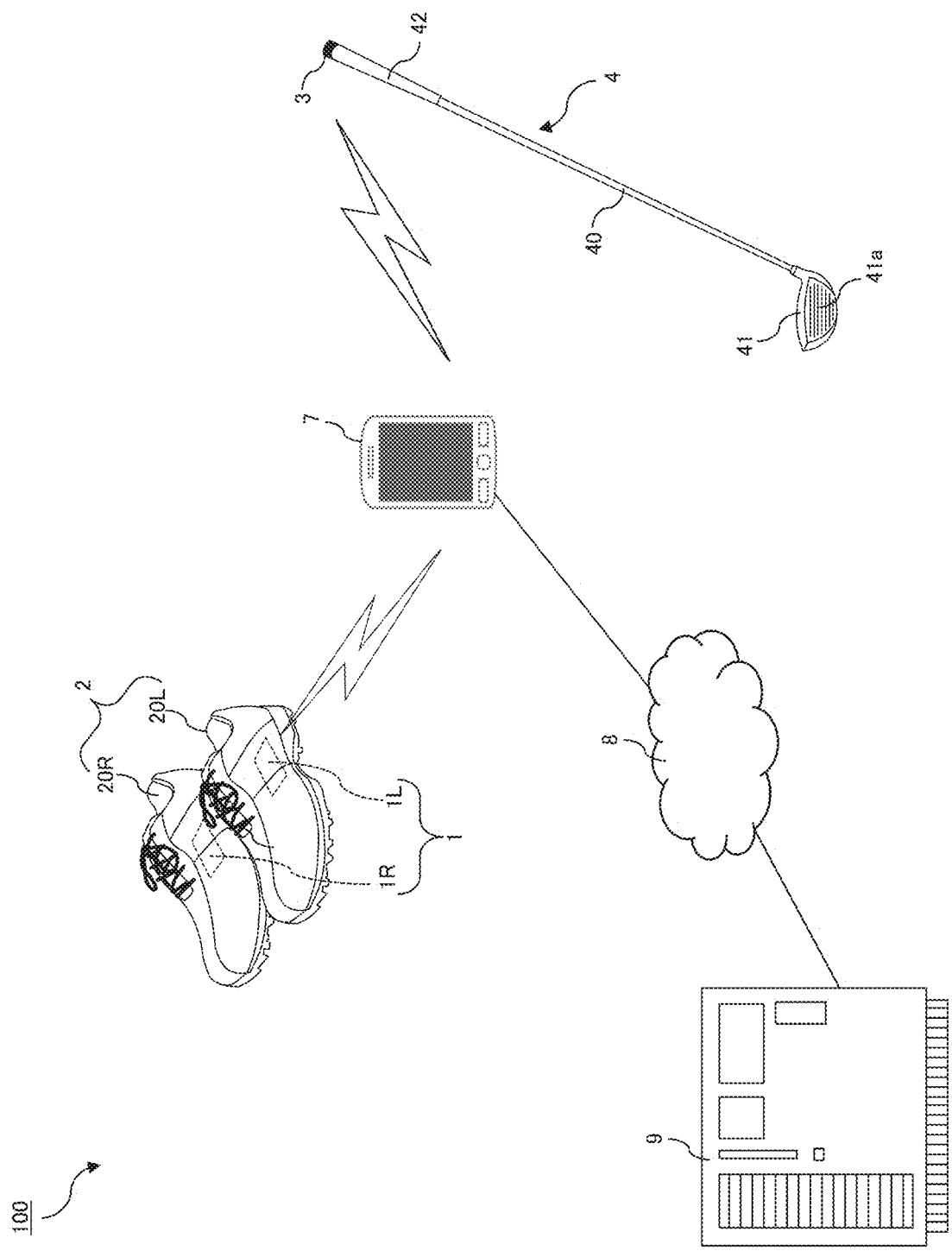
FIG. 1 is a diagram illustrating the overall configuration of a golf measurement system including sensor device-equipped golf shoes according to an embodiment of the present invention.

FIG. 1 is a diagram illustrating the overall configuration of a golf measurement system 100 according to the present embodiment. The golf measurement system 100 is a system that collects and analyzes data pertaining to a shot taken by a golfer (this includes sensor data and club data, which will be described later and will be called "shot data" hereinafter). Although not limited thereto, the shot data is typically collected during a round on a golf course. The golf measurement system 100 includes golf shoes 2 equipped with sensor devices 1, a golf club 4 equipped with a sensor unit 3, and a mobile terminal 7. The golf shoes 2 equipped with the sensor devices 1 and the golf club 4 equipped with the sensor unit 3 are brought onto the golf course by the golfer and used during the round. The mobile terminal 7 is also brought onto the golf course by the same golfer, and is carried and used during the round.

The sensor devices 1 fitted to the golf shoes 2 measure various types of sensor data that enable the orientation of the golfer's feet during shots to be analyzed, and sends that data wirelessly to an external device. The "external device" mentioned here includes the mobile terminal 7. The lie and stance during the shot can be identified, as information of the orientation of the feet, from the sensor data collected by the sensor devices 1. The sensor unit 3 attached to the golf club 4 measures various types of sensor data indicating the state of the golf club 4 during the shot, and sends that data to wirelessly to the external device. The "external device" mentioned here as well includes the mobile terminal 7.

The various types of sensor data collected as described above is used by the mobile terminal 7 to analyze the shot. The analysis results are provided to the golfer through the mobile terminal 7 as appropriate. The golfer can use the analysis results not only when playing the current round, but also when playing in the future (and during practice at driving ranges, golf schools, and so on, in addition to playing rounds on a golf course).

The mobile terminal 7 is connected to a server 9 over a communication network 8 such as the internet. The mobile terminal 7 sends the sensor data obtained from the sensor devices 1 and the sensor unit 3, and data expressing the analysis results thereof (called "analysis data" hereinafter), to the server 9. The server 9 holds a database 9a (see FIG. 5) in which the sensor data and the analysis data is stored, and provides that data as appropriate in response to requests from the mobile terminal 7 or a given computer operated by the golfer.

Next, the configurations of the golf shoes 2 equipped with the sensor devices 1, the golf club 4 equipped with the sensor unit 3, the mobile terminal 7, and the server 9 will be described, after which a golf measurement method carried out using the golf measurement system 100 will be described.

2. Configurations of Various Parts 2-1. Sensor Device-Equipped Golf Shoes

As illustrated in FIG. 1, the golf shoes 2 include a pair of left and right shoes 20L and 20R, which are worn by the golfer during a round. The shoe 20L is worn on the golfer's left foot, and the shoe 20R is worn on the golfer's right foot. The sensor devices 1 are compact and lightweight so as not to interfere with the golfer's play. In the present embodiment, the sensor devices 1 are fixed to the golf shoes 2, but it is also possible to configure the sensor devices 1 to be removable. The sensor devices 1 include a pair of left and right sensor units 1L and 1R, with the sensor unit 1L being fitted to the shoe 20L for the left foot, and the sensor unit 1R being fitted to the shoe 20R for the right foot. Although not limited thereto, in the present embodiment, the sensor units 1L and 1R are embedded into the heel parts of the soles of the shoe 20L and the shoe 20R, respectively.

Figure 2:
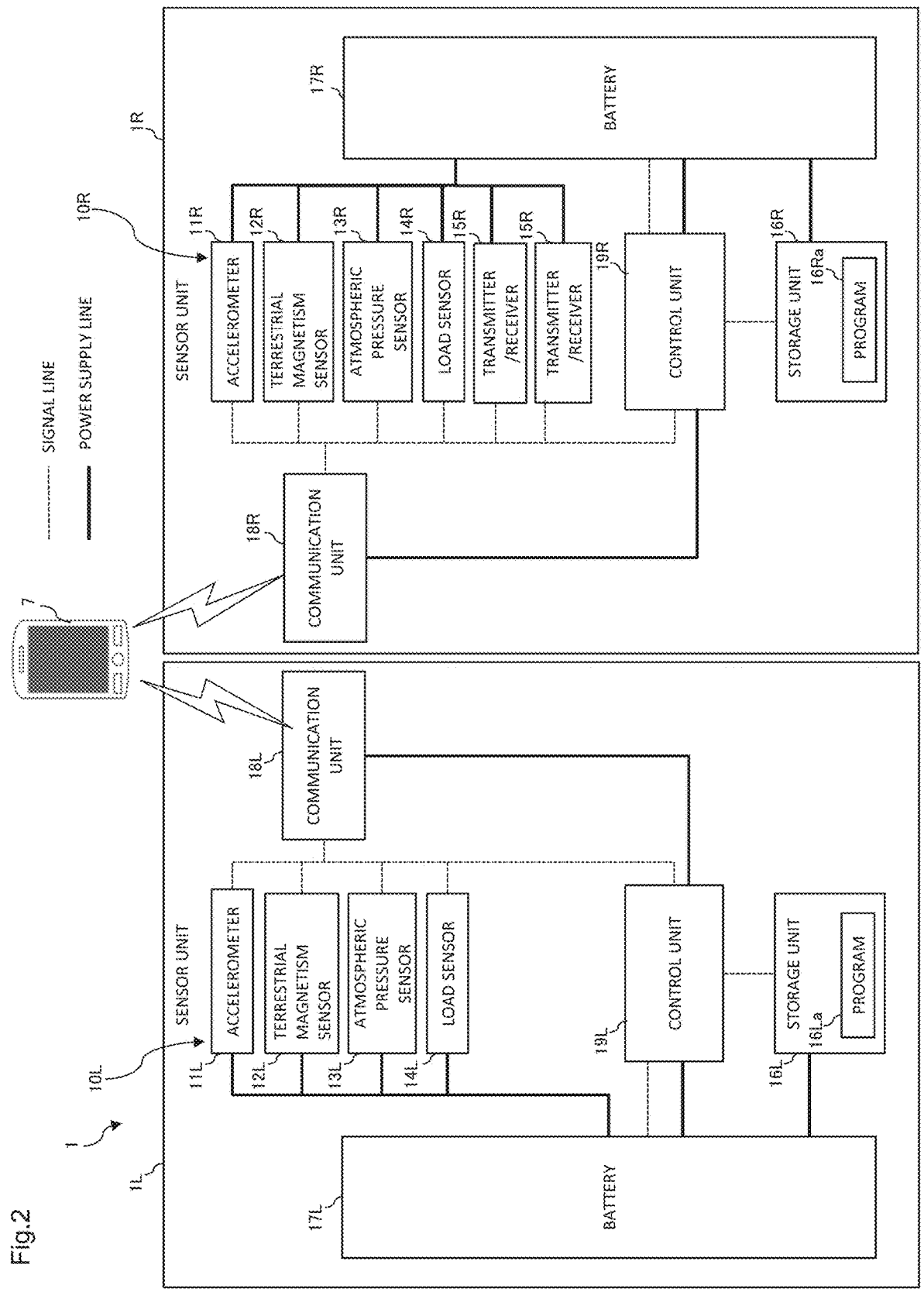
FIG. 2 is a diagram illustrating the electrical configuration of a sensor device fitted to golf shoes.

FIG. 2 is a diagram illustrating the electrical configuration of the sensor devices 1. As illustrated in FIG. 2, the sensor unit 1L includes one or more sensor modules 10L. In the present embodiment, the sensor unit 1L includes an accelerometer 11L, a terrestrial magnetism sensor 12L, an atmospheric pressure sensor 13L, and a load sensor 14L as the sensor modules 10L. Likewise, the sensor unit 1R includes one or more sensor modules 10R. In the present embodiment, the sensor unit 1R includes an accelerometer 11R, a terrestrial magnetism sensor 12R, an atmospheric pressure sensor 13R, a load sensor 14R, and two transmitters/receivers 15R and 15R as the sensor modules 10R. The accelerometer 11L and the terrestrial magnetism sensor 12L can measure sensor data pertaining to the orientation of the shoe 20L for the left foot, and the accelerometer 11R and the terrestrial magnetism sensor 12R can measure sensor data pertaining to the orientation of the shoe 20R for the right foot. Furthermore, the accelerometer 11L, the terrestrial magnetism sensor 12L, the atmospheric pressure sensor 13L, the accelerometer 11 the terrestrial magnetism sensor 12R the atmospheric pressure sensor 13R, and the two transmitters/receivers 15R and 15R can measure sensor data pertaining to the positional relationship between the left and right shoes 20L and 20R.

The accelerometers 11L and 11R are three-axis accelerometers, and the terrestrial magnetism sensors 12L and 12R are three-axis terrestrial magnetism sensors. The two transmitters/receivers 15R and 15R operate in tandem, and function as ultrasonic sensors or radar sensors. Note that coordinate axes are set for the sensor modules 10L and 10R as appropriate. For example, with the three-axis accelerometers 11L and 11R and the three-axis terrestrial magnetism sensors 12L and 12R, it is preferable that the three axes be set to the following directions: (1) a direction matching the vertical direction (gravitational direction) when the golf shoes are placed on a horizontal plane; (2) a direction facing from the heel toward the toe in a horizontal plane when the golf shoes are placed on a horizontal plane; and (3) a direction orthogonal to the directions of both (1) and (2). However, the coordinate axes of the sensor modules 10L and 10R can be set as desired as long as the relative positional relationship of the shoes 20L and 20R is specified in advance.

In addition to the plurality of sensor modules 10L, the sensor unit 1L includes a communication unit 18L, a control unit 19L, a storage unit 16L, and a battery 17L. Likewise, in addition to the plurality of sensor modules 19R, the sensor unit 1R includes a communication unit 18R, a control unit 19R, a storage unit 16R, and a battery 17R. The communication units 18L and 18R are compliant with a wireless communication standard such as Bluetooth (registered trademark) or Wi-Fi (registered trademark), and are capable of wireless communication with external devices compliant with the same standard. The communication units 18L and 18R operate using power supplied from the batteries 17L and 17R, respectively, and wirelessly send the sensor data output from the sensor modules 10L and 10R to an external device such as the mobile terminal 7.

Each of the control units 19L and 19R is constituted by a CPU, ROM, RAM, and the like. The control units 19L and 19R operate using power supplied from the batteries 17L and 17R, respectively, and control the operations of the sensor modules 10L and 10R the communication units 18L and 18R, the storage units 16L and 16R and the batteries 17L and 17R. The storage units 16L and 16R are configured as non-volatile rewritable storage devices such as Flash memory or the like, and can store and delete data using power supplied from the batteries 17L and 17R respectively. Programs 16La and 16Ra are stored in the storage units 16L and 16R, respectively, and the operations described later are executed by those programs 16La and 16Ra being read out and executed by the CPUs of the control units 19L and 19R, respectively. Note that the programs 16La and 16Ra may be stored in the ROM of the control units 19L and 19R respectively, rather than in the storage units 16L and 16R or may be distributed between the two.

The batteries 17L and 17R are power sources that respectively supply power to the sensor modules 10L and 10R, the communication units 18L and 18R, the control units 19L and 19R, and the storage units 16L and 16R, and are controlled to turn on and off by the control units 19L and 19R. The sensor units 1L and 1R include switches (not shown) which can be accessed from outside the golf shoes 2, and the batteries 17L and 17R can be switched on and off by the golfer operating those switches as well. The batteries 17L and 17R may be primary batteries or secondary batteries. The above-described sensor modules 10L, communication unit 18L, control unit 19L, storage unit 16L, and battery 17L are mounted on one or more boards. Likewise, the above-described sensor modules 10R, communication unit 18R, control unit 19R, storage unit 16R, and battery 17R are mounted on one or more boards.

2-2. Golf Club Equipped with Sensor Unit

As illustrated in FIG. 1, the golf club 4 is a typical golf club, including a shaft 40, a head 41 provided on one end of the shaft 40, and a grip 42 provided on the other end of the shaft 40. The head 41 includes a face surface 41a that strikes a golf ball. The sensor unit 3 is compact and lightweight so as not to interfere with the golfer's play. In the present embodiment, the sensor unit 3 is fixed to the golf club 4, but it is also possible to configure the sensor unit 3 to be removable. If the sensor unit 3 is removable, the same sensor unit 3 can be reattached to the golf club 4 to be used for the next shot. In the present embodiment, the sensor unit 3 is attached to end of the grip 42 on the side opposite from the side on which the head 41 is located (also called the "grip end").

Figure 3:
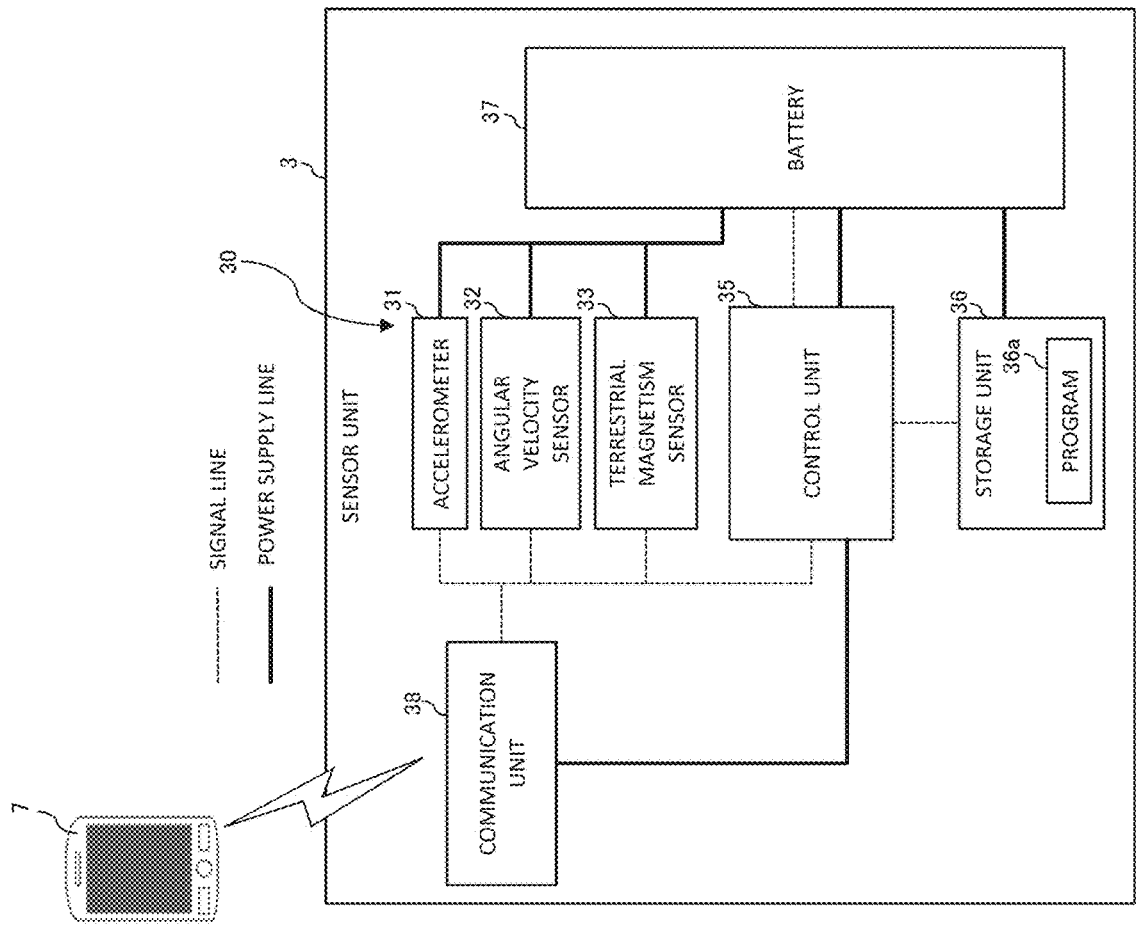
FIG. 3 is a diagram illustrating the electrical configuration of a sensor unit attached to a golf club.

FIG. 3 is a diagram illustrating the electrical configuration of the sensor unit 3. As illustrated in FIG. 3, the sensor unit 3 includes one or more sensor modules 30. In the present embodiment, the sensor unit 3 includes an accelerometer 31, an angular velocity sensor 32, and a terrestrial magnetism sensor 33 as the sensor modules 30. The sensors 31 to 33 constitute an inertia sensor unit. The accelerometer 31 is a three-axis accelerometer, the angular velocity sensor 32 is a three-axis angular velocity sensor, and the terrestrial magnetism sensor 33 is a three-axis terrestrial magnetism sensor.

In addition to the plurality of sensor modules 30, the sensor unit 3 includes a communication unit 38, a control unit 35, a storage unit 36, and a battery 37. The communication unit 38 is compliant with a wireless communication standard such as those mentioned above, and is capable of wireless communication with external devices compliant with the same standard. The communication unit 38 operates using power supplied from the battery 37, and wirelessly sends the sensor data output from the sensor modules 30 to an external device such as the mobile terminal 7.

The control unit 35 is constituted by a CPU, ROM, RAM, and the like. The control unit 35 operates using power supplied from the battery 37, and controls the operations of the sensor modules 30, the communication unit 38, the storage unit 36, and the battery 37. The storage unit 36 is configured as a non-volatile rewritable storage device such as Flash memory or the like, and can store and delete data using power supplied from the battery 37. A program 36a is stored in the storage unit 36, and the operations described later are executed by that program 36a being read out and executed by the CPU of the control unit 35. Note that the program 36a may be stored in the ROM of the control unit 35, rather than in the storage unit 36, or may be distributed between the two.

The battery 37 is a power source that supplies power to the sensor modules 30, the communication unit 38, the control unit 35, and the storage unit 36, and is controlled to turn on and off by the control unit 35. The sensor unit 3 includes a switch (not shown) which can be accessed from outside the golf club 4, and the battery 37 can be switched on and off by the golfer operating that switch as well. The battery 37 may be a primary battery or a secondary battery. The above-described sensor modules 30, communication unit 38, control unit 35, storage unit 36, and battery 37 are mounted on one or more boards.

2-3. Mobile Terminal

Figure 4:
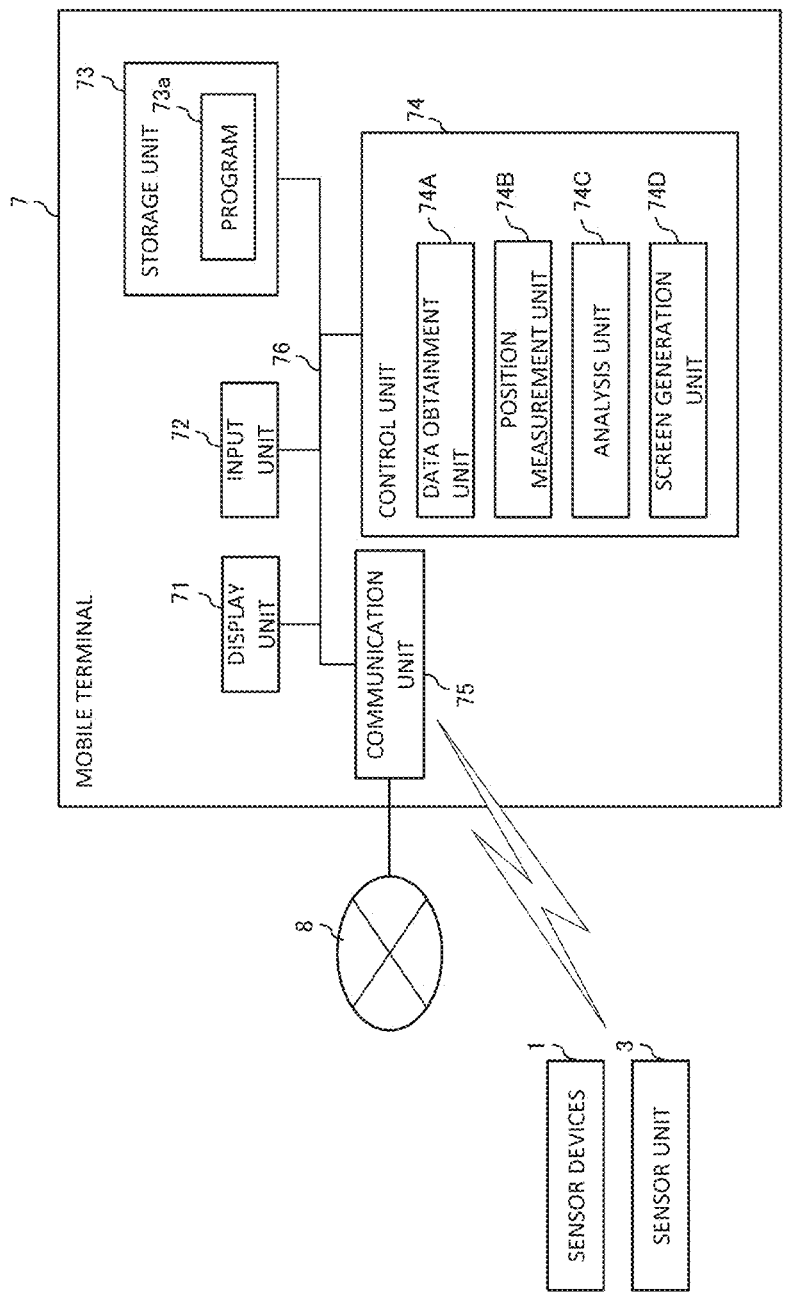
FIG. 4 is a diagram illustrating the electrical configuration of a mobile terminal.

FIG. 4 illustrates the configuration of the mobile terminal 7. The mobile terminal 7 is carried by the golfer, and can be carried to a variety of locations aside from a golf course, such as the golfer's own home, a golf driving range, and a golf school. The mobile terminal 7 uses a computer, such as a smartphone, a tablet computer, a wearable device such as a smartwatch, a laptop computer, or an augmented reality (AR) terminal such as smart glasses, as its hardware, and is constituted by a predetermined application program 73a being installed in the computer. Typically, the program 73a is delivered from an external device to the mobile terminal 7 over the communication network 8, such as the internet, or a network for wireless communication or the like as described above.

As illustrated in FIG. 4, the mobile terminal 7 includes a display unit 71, an input unit 72, a storage unit 73, a control unit 74, and a communication unit 75. These units 71 to 75 are connected to each other by a bus line 76, and are capable of communicating with each other. In the present embodiment, the display unit 71 is constituted by a liquid crystal display or the like, and displays various types of screens, including an analysis result screen W1 (described later), to the golfer. The input unit 72 is constituted by a touch panel, operation buttons, a mouse, a keyboard, and the like, and accepts operations of the mobile terminal 7 from the golfer.

The storage unit 73 is constituted by a non-volatile storage device such as Flash memory or a hard disk, and stores the program 73a. The control unit 74 is constituted by a CPU, ROM, RAM, and the like. The control unit 74 operates as a data obtainment unit 74A, a position measurement unit 74B, an analysis unit 74C, and a screen generation unit 74D by reading out the program 73a from the storage unit 73 and executing the program 73a. The position measurement unit 74B communicates with a satellite positioning system such as a Global Positioning System (GPS), the Quasi-Zenith Satellite System, GLONASS, or the like, and measures position information of the mobile terminal 7 on the basis of signals obtained from that system. The operations of the units 74A to 74D will be described in more detail later.

The communication unit 75 functions as a communication interface that connects the mobile terminal 7 to the communication network 8, such as the internet. The communication unit 75 is compliant with a wireless communication standard such as those mentioned above, and is capable of wireless communication with external devices compliant with the same standard (including the sensor devices 1 and the sensor unit 3).

2-4. Server

Figure 5:
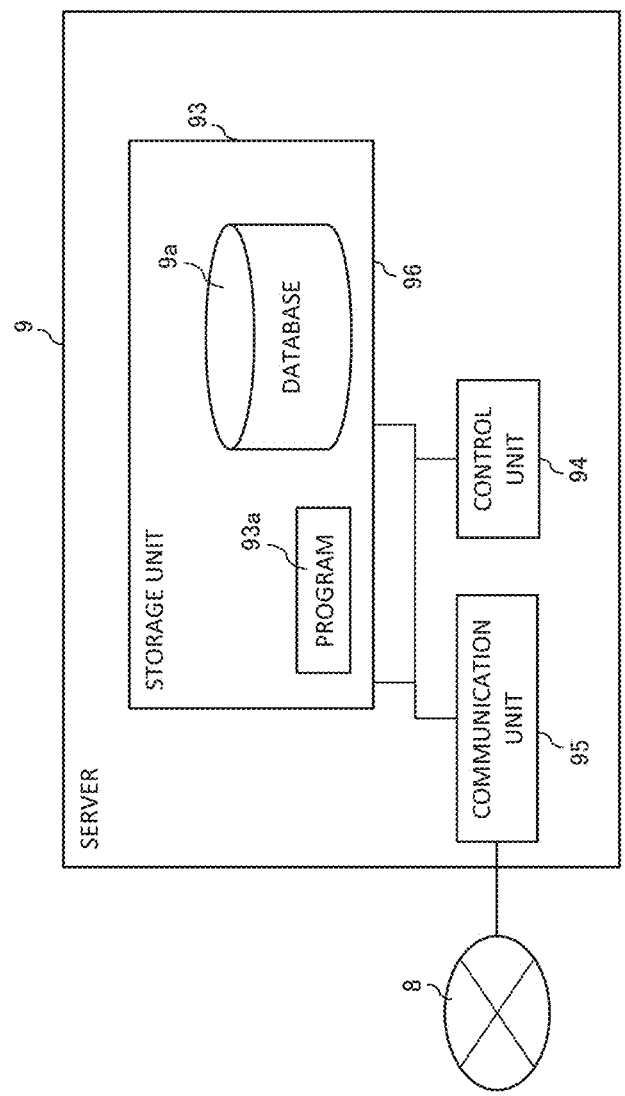
FIG. 5 is a diagram illustrating the electrical configuration of a server.

FIG. 5 illustrates the configuration of the server 9. The server 9 is a server computer uses a server computer, such as a cloud computing server, as its hardware, and is constituted by a program 93a being installed in that computer. The program 93a is a program that causes the server 9 to execute processing that will be described later.

As illustrated in FIG. 5, the server 9 includes a storage unit 93, a control unit 94, and a communication unit 95.

These units 93 to 95 are connected to each other by a bus line 96, and are capable of communicating with each other.

The storage unit 93 is constituted by a non-volatile storage device such as a hard disk, and stores the aforementioned database 9a and the program 93a. The control unit 94 is constituted by a CPU, ROM, RAM, and the like. The control unit 94 executes processing which will be described later by reading out the program 93a from the storage unit 93 and executing the program 93a. The communication unit 95 functions as a communication interface that connects the server 9 to the communication network 8, such as the internet.

3. Flow of Processing by Golf Measurement System

The golf measurement method carried out by the golf measurement system 100 described above will be described next, using a situation where the golfer plays a round on a golf course as an example. First, when starting the round, the golfer operates the switches of the sensor units 1L, 1R and 3 attached to the golf shoes 2 and the golf club 4 to turn the power sources thereof (the batteries 17L, 17R, and 37) on. At this time, the golfer also operates the input unit 72 of the mobile terminal 7 to launch the application program 73a on the mobile terminal 7.

Once these preparations are complete, the golfer, who has equipped the golf shoes 2, uses the golf club 4 to take shots while progressing through the golf course. The golfer may take any number of shots during the round.

Figure 6:
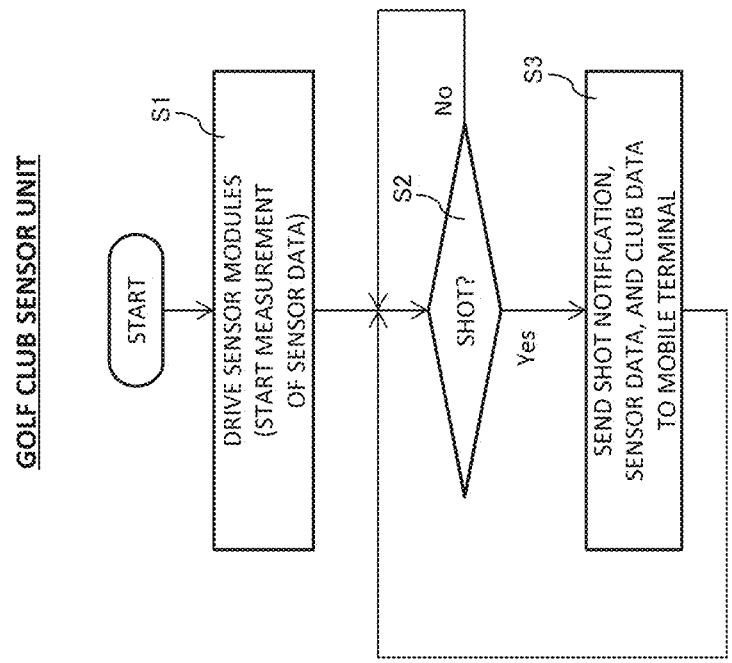
FIG. 6 is a diagram illustrating the flow of processing by the sensor unit attached to the golf club.

In response to the battery 37 being turned on, the sensor unit 3 starts the processing illustrated in FIG. 6. Additionally, in response to the batteries 17L and 17R being turned on, the sensor devices 1 starts the processing illustrated in FIG. 7. Furthermore, in response to the application program 73a being launched, the mobile terminal 7 starts the processing illustrated in FIG. 8.

As illustrated in FIG. 6, the control unit 35 of the sensor unit 3 attached to the golf club 4 first drives the sensor modules 30 (step S1). In response, the sensor modules 30 start measuring the sensor data at predetermined intervals of time. The sensor data sequentially obtained by the sensor modules 30 is stored in the storage unit 36. Note that when the amount of sensor data in the storage unit 36 exceeds the capacity of the storage unit 36, older sensor data is deleted and newer sensor data is saved.

Next, the control unit 35 detects a shot made by the golfer on the basis of the sensor data in the storage unit 36 (step S2). In the present embodiment, acceleration, angular velocity, and terrestrial magnetism data are obtained as the sensor data. The values of the sensor data vary drastically during a shot, when the golf club 4 to which the sensor unit 3 is attached is swung and collides with the golf ball. The timing of the shot can therefore be detected by detecting such drastic variations from the sensor data. Although the sensor data in the storage unit 36 is stored sequentially as described above, the control unit 35 determines whether or not the golfer has taken a shot on the basis of unprocessed sensor data in the storage unit 36. Once it is determined that a shot has been made, the process moves to step S3.

In step S3, the control unit 35 sends a notification that a shot has been taken (called a "shot notification" hereinafter) to the mobile terminal 7 through the communication unit 38. The shot notification includes information indicating the time at which the shot was taken (called a "shot time" hereinafter). At this time, the control unit 35 extracts the sensor data from before and after the shot time, from the sensor data stored in the storage unit 36, and sends the extracted sensor data along with the shot notification to the mobile terminal 7 through the communication unit 38. The control unit 35 also sends the club data along with the shot notification to the mobile terminal 7 through the communication unit 38 at this time. The club data is information, stored in the storage unit 36 or the ROM, that specifies the type of the golf club 4, and is information indicating, for example, the model number and/or the club number. Thereafter, the process returns to step S2, where steps S2 to S3 are repeated until the battery 37 is turned off. When the battery 37 is turned off, the sensor modules 30 also stop measuring the sensor data.

Figure 7:
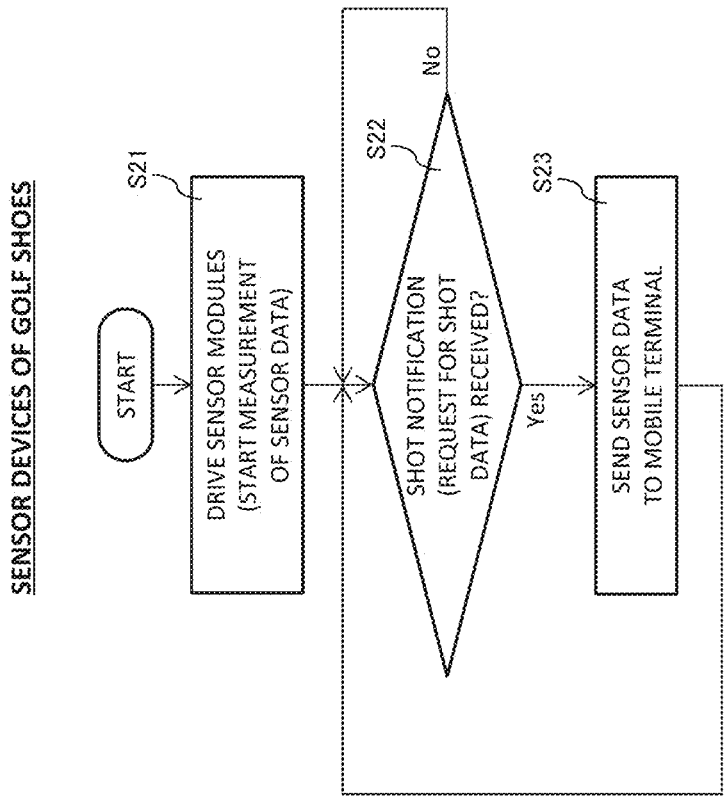
FIG. 7 is a diagram illustrating the flow of processing by the sensor device fitted to the golf shoes.

On the other hand, the sensor devices 1 of the golf shoes 2 carry out the processing illustrated in FIG. 7, in parallel with the processing illustrated in FIG. 6. Of the sensor units 1L and 1R included in the sensor devices 1, processing carried out by the sensor unit 1L provided for the left foot will be described in detail hereinafter. However, in the present embodiment, the sensor units 1L and 1R carry out equivalent processing, and thus the following descriptions can be applied to the sensor unit 1R by changing "L" to "R" and "left" to "right".

First, the control unit 19L of the sensor unit 1L drives the sensor modules 10L (step S21). In response, the sensor modules 10L start measuring the sensor data at predetermined intervals of time. The sensor data sequentially obtained by the sensor modules 10L is stored in the storage unit 16L. Note that when the amount of sensor data in the storage unit 16L exceeds the capacity of the storage unit 16L, older sensor data is deleted and newer sensor data is saved.

Next, the control unit 19L stands by for the shot notification to be send from the mobile terminal 7 through the communication unit 18L (step S22). As described above, the shot notification is first sent to the mobile terminal 7 from the sensor unit 3 of the golf club 4 (step S3). The notification is then transferred from the mobile terminal 7 to the sensor devices 1, as will be described later (step S33). However, in another embodiment, the configuration can be such that the shot notification is sent directly from the sensor unit 3 to the sensor devices 1 over a local wireless network, without going through the mobile terminal 7.

Upon receiving the shot notification, the control unit 19L extracts the sensor data from before and after the shot time, from the sensor data stored in the storage unit 16L, and sends the extracted sensor data to the mobile terminal 7 through the communication unit 18L (step S23). In this sense, the shot notification sent to the sensor devices 1 from the mobile terminal 7 is a request for the sensor data from when the shot was taken. Thereafter, the process returns to step S22, where steps S22 to S23 are repeated until the batteries 17 are turned off. When the batteries 17 are turned off, the sensor modules 10L also stop measuring the sensor data.

Figure 8:
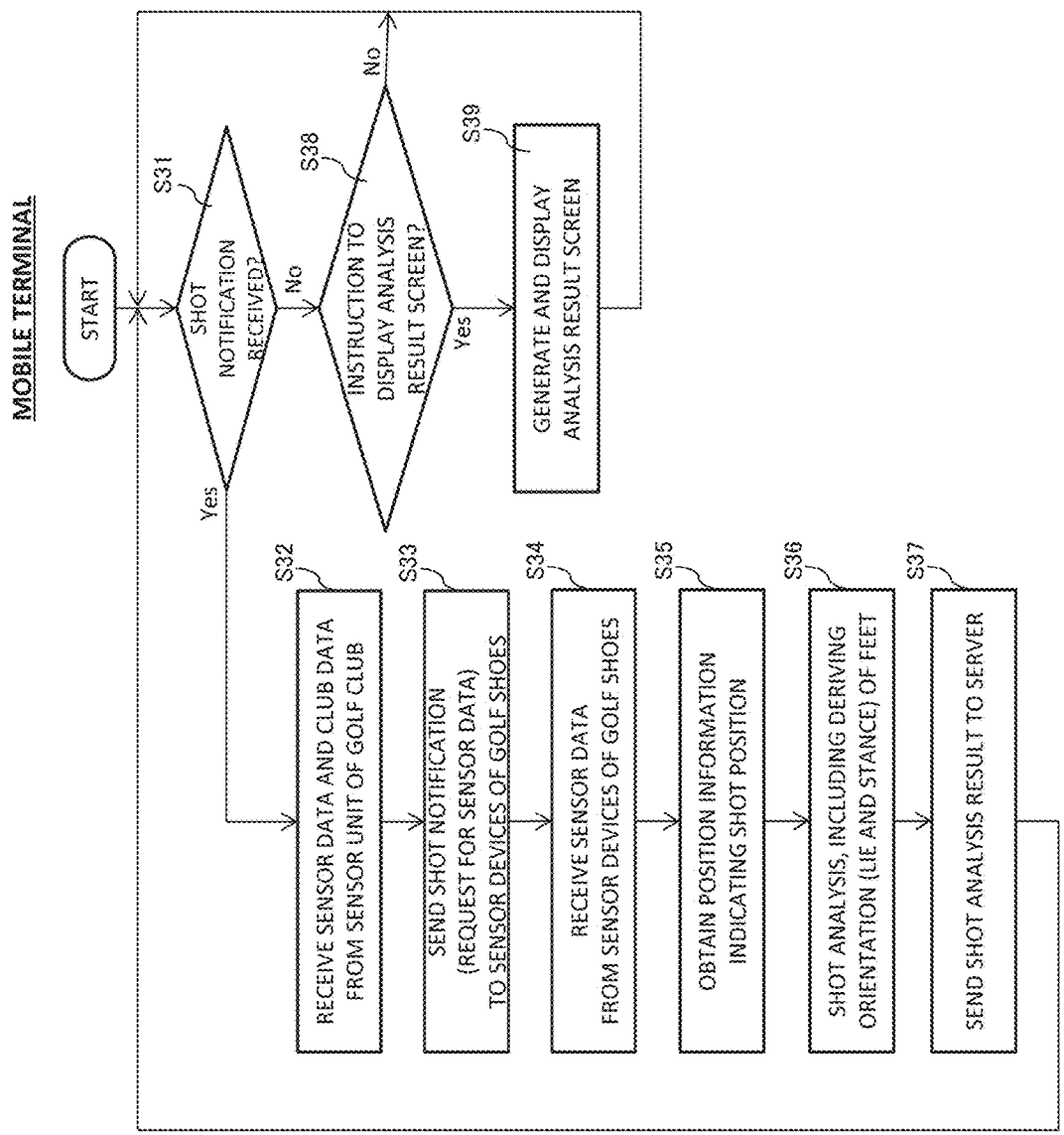
FIG. 8 is a diagram illustrating the flow of processing by the mobile terminal.

The mobile terminal 7 carries out the processing illustrated in FIG. 8 in parallel with the processing illustrated in FIGS. 6 and 7. First, the data obtainment unit 74A determines whether a shot notification has been sent from the golf club 4 (step S31). If the data obtainment unit 74A has received a shot notification corresponding to the above-described step S3 through the communication unit 75, the process moves to step S32, whereas if such a shot notification has not been received, the process moves to step S38.

In step S32, the data obtainment unit 74A receives the sensor data and club data from before and after the shot time, which are sent along with the shot notification corresponding to the above-described step S3, from the sensor unit 3 of the golf club 4, through the communication unit 75. The sensor data and club data from the sensor unit 3 are stored in the storage unit 73.

Next, in step S33, the data obtainment unit 74A sends the shot notification from the mobile terminal 7, obtained in step S31, to the sensor devices 1 of the golf shoes 2 through the communication unit 75. The data obtainment unit 74A then receives the sensor data from before and after the shot time, sent in correspondence with the above-described step S23, from the sensor devices 1 through the communication unit 75 (step S34). The sensor data from the sensor devices 1 is stored in the storage unit 73.

Next, in step S35, the position measurement unit 74B measures position information of the mobile terminal 7. In the present embodiment, the position information is obtained as latitude and longitude information. Note that step S35 is executed immediately after the shot notification has been received from the sensor unit 3 of the golf club 4. As such, this position information is obtained as position information indicating the position where the shot was taken (called a "shot position" hereinafter). Alternatively, the mobile terminal 7 may consecutively measure the position information after the application program 73a is launched, store that position information in the storage unit 73, and then specify the position information indicating the shot position on the basis of the shot time. The position information of the shot position is stored in the storage unit 73 in association with the shot notification obtained in step S31, the sensor data and club data obtained in step S32, and the sensor data obtained in step S34.

Next, in step S36, the analysis unit 74C analyzes the immediately-previous shot on the basis of the shot data pertaining to the shot, obtained in the immediately-previous steps S32, S34, and S35 and stored in the storage unit 73. Here, the orientation of the golfer's feet during the shot is analyzed. In the present embodiment, the analysis unit 74C derives values for a variety of parameters L, $\theta_1$ to $\theta_3$, $\theta_R$, and $\theta_L$ as information indicating the orientation of the feet. The method for deriving these values will be described later. However, L represents the distance between the left and right feet; $\theta_1$, the direction (heading) of the stance; $\theta_2$, the height difference between the left and right feet; $\theta_3$, the angle of slope of the left and right feet in the forward-backward direction; and $\theta_L$ and $\theta_R$, the angle of aperture of the left and right feet (see FIGS. 10 to 12). The analysis unit 74C also derives the identified lie and stance for the shot from the values of the parameters L, $\theta_1$ to $\theta_3$, $\theta_R$, and $\theta_L$, as information indicating the orientation of the feet. The lie information is specified as, for example, "horizontal", "toe-up", "toe-down", "right foot up", "left foot up", "horizontal, right foot up", "horizontal, left foot up", "toe-up, right foot up". "toe-up, left foot up", "toe-down, right foot up", "toe-down, left foot up", and so on. The stance information is specified as the direction (heading) of the stance.

Aside from the information of the orientation of the feet described above, the analysis unit 74C also derives the following information. Specifically, the analysis unit 74C derives loads acting on the soles of the golfer's left and right feet at the time of the shot, on the basis of the sensor data obtained from the load sensors 14L and 14R of the golf shoes 2. These loads may be derived as a distribution of the pressure acting on the soles of the left and right feet. On the basis of this load information, the analysis unit 74C derives information such as how the golfer is distributing his or her body weight between both feet when addressing the ball and during the swing, whether his or her body weight is more on the toes or the heels, and so on.

Additionally, on the basis of the sensor data obtained from the accelerometer, angular velocity, and terrestrial magnetism sensors 31 to 33 of the golf club 4, the analysis unit 74C derives the trajectory of the golf club 4 (inside-out, straight, outside-in, or the like), the velocity and direction the head 41 is facing at the time of impact (including the angle of the face surface 41a), the point of impact of the golf ball on the face surface 41a, and the tempo of the swing.

The above-described shot analysis data (including the information of the orientation of the feet) is saved in the storage unit 73. The above-described analysis data, aside from the information of the orientation of the feet, which has been derived by the analysis unit 74C, is associated with the information of the orientation of the feet, which includes the lie and the stance, and thus serves as information that can be effectively used during golf practice.

Next, in step S37, the analysis unit 74C sends the above-described analysis data to the server 9 through the communication unit 75. In the server 9, the control unit 94 receives the information indicating the analysis results through the communication unit 95 and stores that information in the database 9a. At this time, information identifying the golfer (called a "golfer ID" hereinafter) is stored in the database 9a in association with the analysis data. The golfer ID is sent from the mobile terminal 7 to the server 9 along with the analysis data.

Once step S37 ends, the process returns to step S31. Steps S32 to S37 are executed again when the golfer takes his or her next shot.

Step S38 will be described next. As described above, step S38 is a step executed when the shot notification has not been received in step S31. In step S38, the screen generation unit 74D accepts an instruction to display the analysis result screen W1 from the golfer. After launching the application program 73a, the golfer can enter this instruction at any desired time through the input unit 72. The analysis result screen W1 is a screen that displays the analysis results obtained by the analysis unit 74C in step S36. Accordingly, if no shots have been taken yet, no shot analysis results are displayed in the screen W1. However, after a shot or shots have been taken, the analysis results of all of the shots taken up until that point are displayed in the screen W1.

Figure 9:
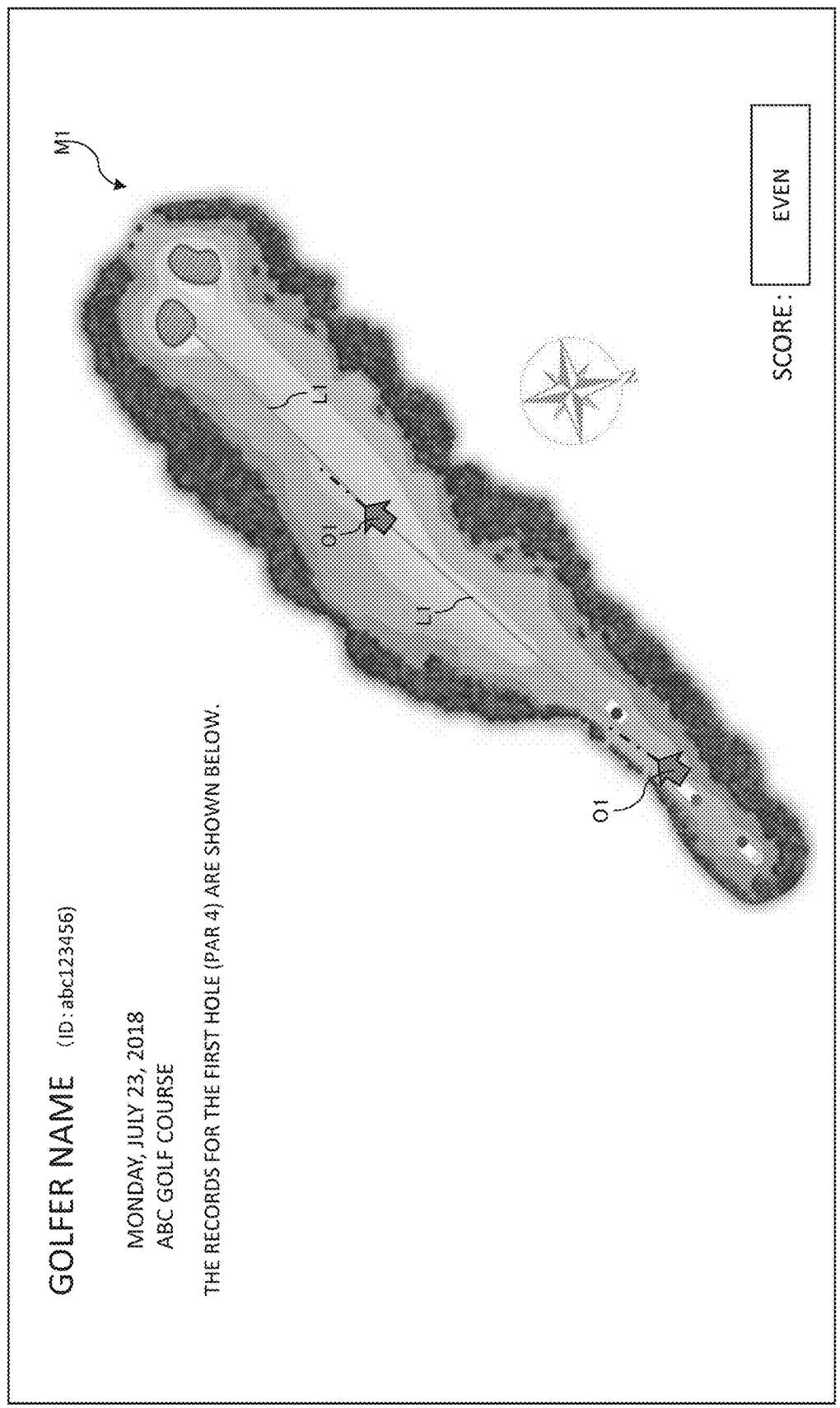
FIG. 9A is a diagram illustrating an example of a shot analysis result screen.
FIG. 9B is a diagram illustrating another example of a shot analysis result screen.

Upon detecting that an instruction to display the analysis result screen W1 has been entered, the screen generation unit 74D generates the analysis result screen W1 and displays that screen in the display unit 71 (step S39). The analysis result screen W1 is generated on the basis of the analysis data from the analysis unit 74C, which is stored in the storage unit 73. FIG. 9A is an example of the analysis result screen W1. As illustrated in FIG. 9A, information of the lie and stance, serving as the information of the orientation of the feet, is displayed in the analysis result screen W1 for each shot.

Information indicating the club used for each shot and the flight distance is also displayed in the analysis result screen W1. The club that was used is identified on the basis of the club data in the storage unit 73. The flight distance is identified on the basis of the position information of the shot focused on in the storage unit 73, and of the shot that follows thereafter. Although not illustrated in detail in FIG. 9A, other analysis results from the analysis unit 74C, which are stored in the storage unit 73, are also displayed in the analysis result screen W1. For example, it is preferable that information such as the trajectory of the golf club 4 (inside-out, straight, outside-in, and so on), the direction the head 41 is facing at the time of impact, the velocity of the head 41 at the time of impact, the point of impact, the tempo of the swing, the body weight distribution (the percentage of the load acting on the right foot, the percentage of the load acting on the toe side, and so on), and the like be displayed as analysis results.

The analysis result screen W1 displays the above-described information altogether for each hole. The data obtainment unit 74A can access a predetermined server over the communication network 8, such as the internet, and download information of the golf course where the golfer is presently playing (including map information of all the holes) on the basis of the current position information measured by the position measurement unit 74B. By verifying the map information of the holes with the position information at the time of each shot, the hole where each shot has been taken can be identified. The screen generation unit 74D can also generate an image in which an object O1 indicating the shot position is superimposed on a map M1 of the hole, and display that image in the analysis result screen W1. The object O1 indicating the shot position may be in a format expressing the direction of the stance at that shot position, or an object expressing the direction of the stance at that shot position may be arranged in the vicinity of the object O1. In the example illustrated in FIG. 9B, a flight line L1 connecting an object O1 with another object O1 is also displayed. Additionally, although the object O1 and the line L1 are not shown on the green in the example illustrated in FIG. 9B, those items may of course be displayed.

The analysis result screen W1 also displays information of the score for each hole and information of the score for the round. This information may be specified from inputs made by the golfer, or may be specified on the basis of information of the golf course (including part information) and the shot data.

The golfer can understand the details of how he or she played during the round by viewing the above-described analysis result screen W1. The analysis result screen W1 may be provided during the round or after the round, depending on the timing at which the golfer instructs the analysis result screen W1 to be displayed. Once step S39 ends, the process returns to step S31.

Once the round of golf ends, the golfer operates the switches on the sensor units 1L, 1R, and 3 and turns the power sources (the batteries 17L, 17R, and 37) off, and furthermore operates the input unit 72 to terminate the application program 73a. The process of FIG. 8 ends upon the golfer performing the operation to terminate the application program 73a.

The parameters indicating the information of the orientation of the feet will be described in detail hereinafter.

3-1. L: Distance Between Left and Right Feet

The distance L between the left and right feet is measured by the ultrasonic sensor or radar sensor included in the transmitters/receivers 15R. To be more specific, the transmitters/receivers 15R emit ultrasonic waves or radar pulses, and the distance L is derived by measuring the amount of time until reflected waves reflected by a target object, i.e., the left shoe 20L. Although a measurement method based on the right foot is described here, the method may be based on either the left or the right foot. The method is not limited to the distance L, and can be applied similarly when deriving other parameters as well.

The ultrasonic sensor or radar sensor can be used to derive $\theta_1$ and $\theta_2$, which will be described later. As such, it is desirable that the measurement of the distance L and the measurement of $\theta_1$ and $\theta_2$ do not interfere with each other. For example the measurement times may be staggered, or pulses having different frequencies may be used. Furthermore, a transmitter/receiver may be attached to the target object, i.e., the sensor unit 1L of the left shoe 20L, in order to improve the accuracy of the measurement of the distance L. In this case, the additional transmitter/receiver is configured to return pulses of a different frequency when receiving pulses from the transmitters/receivers 15R. In this case, the transmitters/receivers 15R can distinguish the reflected waves from the additional transmitter/receiver from reflected waves from unknown reflection positions, and the distance L can be accurately derived on the basis of the reflected waves from the additional transmitter/receiver.

3-2. $\theta_1$: Direction (Heading) of Stance

Figure 10:
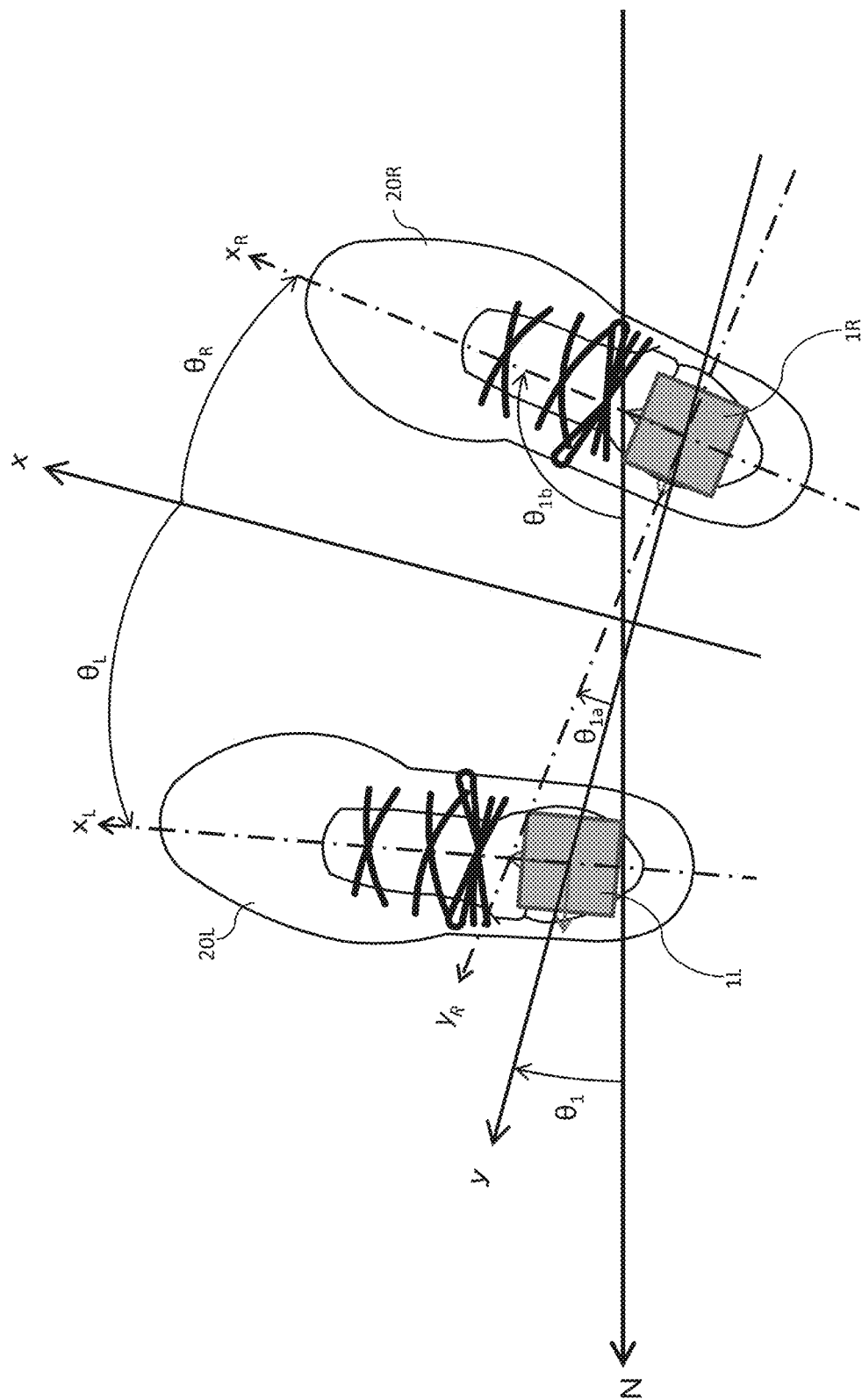
FIG. 10 is a diagram illustrating parameters indicating the orientation of feet.

As illustrated in FIG. 10, the direction (heading) $\theta_1$ of the stance is an angle formed by an axis connecting the heels of the left and right shoes 20L and 20R (an axis oriented from the sensor unit 1R of the right foot toward the sensor unit 1L of the left foot; the y axis, in FIG. 10), and the direction of north (the N axis, in FIG. 10), when viewed from the vertical direction. In the present embodiment, this is calculated through the equation $\theta_1 = \theta_{1b} - 90° - \theta_{1a}$.

$\theta_{1b}$ is the angle formed by an $x_R$ axis oriented from the heel to the toe of the right foot shoe 20R and the direction of north (the N axis) when viewed from the vertical direction, and is measured by the terrestrial magnetism sensor 12R. $\theta_{1a}$ is the direction of the left foot sensor unit 1L relative to the right foot sensor unit 1R when viewed from the vertical direction. Various methods can be used to measure $\theta_{1a}$, such as measuring using the ultrasonic sensors or the radar sensors included in the plurality of transmitters/receivers 15R and 15R. In other words, ultrasonic waves or radar pulses are emitted from the transmitters/receivers 15R and 15R, which are spaced at a predetermined interval, and the amount of time until the reflected waves reflected by a target object, i.e., the left shoe 20L, return to the transmitters/receivers 15R is measured. This makes it possible to measure the distances from each of the transmitters/receivers 15R to the left shoe 20L, which in turn makes it possible to use the principle of triangulation to measure the position and heading of the left foot sensor unit 1L relative to the right foot sensor unit 1R.

However, there are situations where the foregoing method cannot accurately identify the reflection position of the ultrasonic waves or radar pulses. The phase-comparison monopulse technique can therefore also be used to measure $\theta_{1a}$. In this case, a transmitter is provided in the left foot sensor unit 1L. In this case, the right foot transmitters/receivers 15R and 15R may be simple receivers. The ultrasonic waves or radar pulses emitted from the left foot transmitter are received by the right foot receivers 15R and 15R at predetermined intervals, and $\theta_{1a}$ is then derived on the basis of the phase difference between the signals received by the receivers 15R and 15R. In this case, from the standpoint of accuracy, it is desirable that the transmitter be embedded so as to be aligned with the direction of a reference line facing straight to the right from the sensor unit 1L. Furthermore, it is desirable that the receivers 15R and 15R be embedded at locations that are aligned with the direction of a reference line facing straight to the left from the sensor unit 1R and that are equal distances from that reference line.

A method of measuring a three-dimensional position of the target object using magnetism, such as that disclosed in JP 1987-38301A, can be used as another method for measuring $\theta_1$. According to this method, a three-dimensional position is derived, which means that $\theta_2$, $\theta_3$, $\theta_L$, and L can be measured at the same time as $\theta_1$.

Furthermore, an inertia sensor attached to the grip 42, the head 41, or the like can also be used to measure the direction (heading) of the face, and that value can then be used as $\theta_1$. However, the direction of the stance and the direction of the face are not necessarily the same. For example, these two directions will differ if the golfer intentionally holds the club with the face open. Beginners may also unintentionally have different directions between the stance and the face. As such, it is preferable that $\theta_1$ be measured by the sensor devices 1 attached to the golf shoes 2 as described above. However, even if $\theta_1$ is based on the direction of the face, the direction in which the golfer is attempting to hit the ball with respect to the golf course can be understood. As such, $\theta_1$ can be used as feedback information for course management, for example.

3-3. $\theta_L$ and $\theta_R$: Angle of Aperture of Left and Right Feet

As illustrated in FIG. 10, $\theta_L$ is the direction of an $x_L$ axis oriented from the heel to the toe of the left foot shoe 20L when viewed in the vertical direction, and is measured by the left terrestrial magnetism sensor 12L. Likewise. $\theta_R$ is the direction of an $x_R$ axis oriented from the heel to the toe of the right foot shoe 20R when viewed in the vertical direction, and is measured by the right terrestrial magnetism sensor 12R. $\theta_L$ and $\theta_R$ are perpendicular to the existing y axis, and are derived using an x axis present in the horizontal plane as a reference.

3-4. $\theta_2$: Height Difference Between Left and Right Feet

Figure 11:
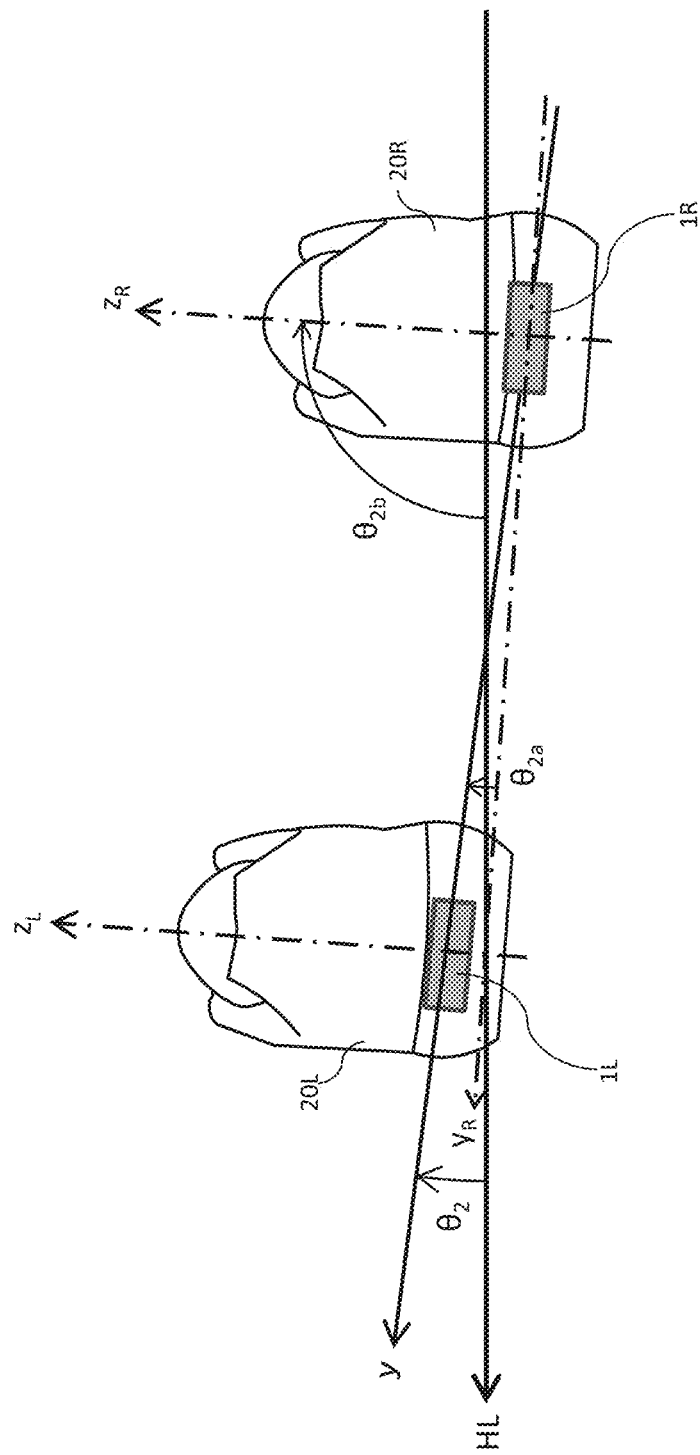
FIG. 11 is a diagram illustrating other parameters indicating the orientation of feet.

As illustrated in FIG. 11, $\theta_2$ is an angle formed by an axis connecting the heels of the left and right shoes 20L and 20R (an axis oriented from the sensor unit 1R of the right foot toward the sensor unit 1L of the left foot; the y axis, in FIG. 11), and a horizontal line HL when viewed from the horizontal direction. This serves as a parameter for evaluating the height difference between the left and right feet. In the present embodiment, this is calculated through the equation $\theta_2 = \theta_{2b} - 90° + \theta_{2a}$.

$\theta_{2b}$ is an angle formed by a $z_R$ axis and the horizontal line HL when viewed from the horizontal direction, and is measured by the accelerometer 11R. The $z_R$ axis is an axis extending from the heel, and is an axis extending vertically upward (relative to the gravitational direction) when the right foot shoe 20R is located on a horizontal plane. $\theta_{2a}$ is the direction of the left foot sensor unit 1L relative to the right foot sensor unit 1R when viewed from the horizontal direction. Various methods can be used to measure $\theta_{2a}$, such as measuring using the ultrasonic sensors or the radar sensors in the same manner as when measuring $\theta_{1a}$. Note that two sets of ultrasonic sensors or radar sensors are required for measuring the heading $\theta_{1a}$ and the elevation angle $\theta_{2a}$.

Deriving $\theta_2$ from the output values from the left and right atmospheric pressure (absolute pressure) sensors 13L and 13R can be used as another method for measuring $\theta_2$. For example, using atmospheric pressure sensors having a height difference (elevation difference) of several tens of cm and a resolution of less than or equal to several cm as the atmospheric pressure sensors 13L and 13R makes it possible to measure the height difference (distance) between the left and right sensor units 1L and 1R $\theta_2$ can then be derived geometrically from the distance L, the width of the stance (using a typical value or a value entered by the golfer), and the height difference (distance).

3-5. $\theta_3$: Angle of Slope in Forward-Backward Direction

Figure 12:
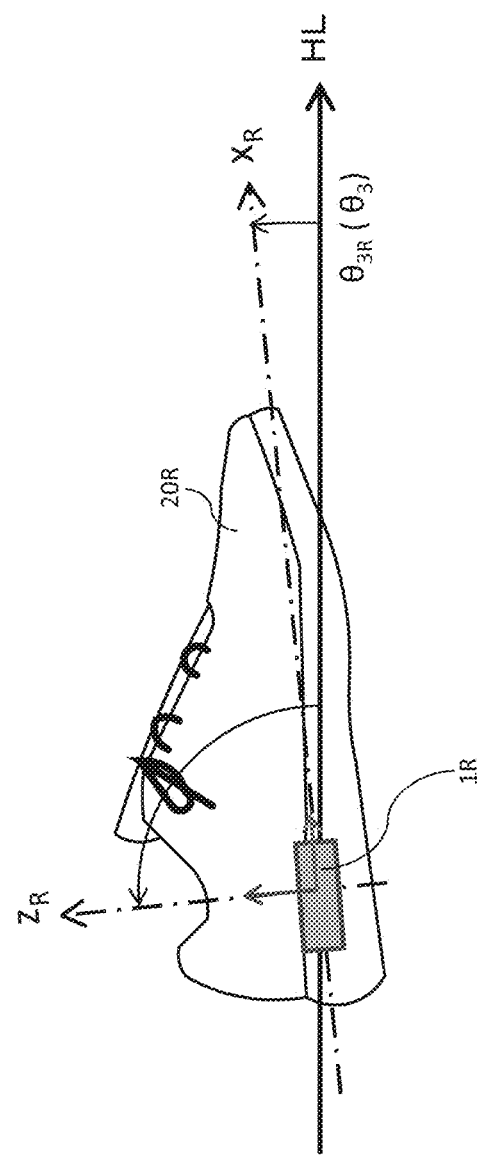
FIG. 12 is a diagram illustrating still other parameters indicating the orientation of feet.

As illustrated in FIG. 12, $\theta_{3R}$ is an angle formed by an axis, parallel to the sole, oriented from the heel toward the toe of the right foot shoe 20R (an axis oriented toward the toe from the sensor unit 1R) and the horizontal line HL, when viewed in the horizontal direction. Likewise, $\theta_{3L}$ is an angle formed by an axis, parallel to the sole, oriented from the heel toward the toe of the left foot shoe 20L (an axis oriented toward the toe from the sensor unit 1L) and the horizontal line HL, when viewed in the horizontal direction. $\theta_{3R}$ can be measured by the accelerometer 11R, and $\theta_{3L}$ can be measured by the accelerometer 11L. $\theta_3$, which indicates the angle of slope of the feet in the forward-backward direction, may match either $\theta_{3L}$ or $\theta_{3R}$, or may be the average thereof (a simple average or a weighted average).

4. Variations

An embodiment of the present invention has been described thus far. However, the present invention is not intended to be limited to the above-described embodiment. Many variations can be made thereon without departing from the essential spirit of the present invention. The following variations are possible, for example. The content of the following variations can also be combined as appropriate.

4-1.

The golf measurement system 100 can be used for measurement not only when playing at a golf course, but also when playing at a driving range.

4-2.

In the foregoing embodiment, the sensor devices 1, the sensor unit 3, and the mobile terminal 7 communicate over wireless connections. However, at least some of these devices may communicate over wired connections. In this case, for example, the sensor data measured during a round may be saved in the storage units 16L and 16R of the sensor devices 1, and the sensor data may then be passed to the mobile terminal 7 over a wired connection later for analysis. The same applies to the communication between the sensor unit 3 and the mobile terminal 7.

4-3.

In the foregoing embodiment, the sensor devices 1 of the golf shoes 2 send the sensor data to the mobile terminal 7 in response to a request from the mobile terminal 7. However, the sensor data, which is continually measured, may be sent to the mobile terminal 7 periodically, rather than waiting for a request from the mobile terminal 7. Additionally, the request for the sensor data issued from the mobile terminal 7 to the sensor devices 1 may be made on the basis of instructions entered by the golfer into the mobile terminal 7 before and after the shot time, rather than being carried out in accordance with the shot time specified on the basis of the sensor data pertaining to the state of the golf club 4.

Additionally, in the foregoing embodiment, the sensor devices 1 of the shoes 2 extract the sensor data before and after the shot time on the basis of the shot time included in the shot notification. However, the sensor devices 1 may extract the sensor data from before and after the shot by going back a predetermined amount of time from the time at which the shot notification, which is sent from the sensor unit 3 of the golf club 4 through the mobile terminal 7, or sent in real time without going through the mobile terminal 7, when a shot is taken, was received.

4-4.

Slope sensors can be attached instead of the accelerometers 11L and 11R.

Using such slope sensors makes it possible to measure the slopes of the left and right shoes 20L and 20R in the forward-backward direction.

4-5.

In the foregoing embodiment, the control units 19L and 19R of the sensor devices 1 send the sensor data measured by the sensor modules 10L and 10R as-is to the mobile terminal 7. However, the original sensor data may be processed by the control units 19L and 19R, and the process data may then be output to an external device such as the mobile terminal 7. For example, the control units 19L and 19R may analyze the orientation of the feet on the basis of the sensor data, derive the above-described values of the parameters L, θ₁ to θ₃, θ_R, and θ_L and the information of the lie and the stance during the shot as the analysis results, and then output that information.

4-6.

In the foregoing embodiment, the mobile terminal 7 analyzes the shots in various ways, and sends that analysis data along with the sensor data to the server 9 for storage. However, the various analysis processes carried out by the analysis unit 74C may be executed by the control unit 94 of the server 9 on the basis of the sensor data from the mobile terminal 7. Then, the golfer may access the server 9 using the mobile terminal 7 or a desired computer she or he operates him or herself, download the analysis data including the analysis result screen W1 from the server 9, and confirm that analysis data.

4-7.

In the foregoing embodiment, the sensor units 1L and 1R are fitted to the left and right shoes 20L and 20R, respectively. However, it is also possible to attach a sensor unit only to one shoe. Even in such a case, sensor modules such as those described above make it possible to specify the simple orientation of both feet, the positional relationship between both feet, and so on.

4-8.

In the foregoing embodiment, the heading of the stance is derived as the information of the stance. However, the direction of the golfer's stance with respect to the intended striking direction, such as a "square stance", an "open stance", a "closed stance", and so on, may be derived as the stance information. The golfer's intended striking direction can be entered in the mobile terminal 7 by the golfer him or herself, and can be identified from the direction of the face surface 41a when addressing the ball, the trajectory of the golf club 4 during the shot, and so on. Based on the above-described distance L, information such as "wide stance" or "narrow stance" can also be derived as the stance information.

DESCRIPTION OF REFERENCE NUMERALS

1 Sensor Device
1L, 1R Sensor Unit
10L, 10R Sensor Module
11L, 11R Accelerometer
12L, 12R Terrestrial Magnetism Sensor
13L, 13R Atmospheric Pressure Sensor
15R, 15R Transmitter/Receiver (Ultrasonic Sensor, Radar Sensor)
18L, 18R Communication Unit
19L, 19R Control Unit
2 Golf Shoes
20L, 20R Pair Of Left And Right Shoes
3 Sensor Unit
4 Golf Club
7 Mobile Terminal (Analysis Device)
71 Display Unit
74 Control Unit
74A Data Obtainment Unit
74B Position Measurement Unit
74C Analysis Unit
74D Screen Generation Unit
9 Server (Analysis Device)

What is claimed is:

1. A golf measurement system comprising:
sensor device-equipped golf shoes including a first shoe and a second shoe of a pair of the golf shoes to be worn by a golfer; and
a sensor device attached to the golf shoes; and
an external device configured to be carried by the golfer,
wherein the sensor device includes:
one or more sensor modules configured to measure sensor data pertaining to at least one of an orientation of the first shoe when the golfer takes a shot, an orientation of the second shoe when the golfer takes a shot, and a positional relationship between the first shoe and the second shoe when the golfer takes the shot;
a communication unit connected to the external device wirelessly or over a wire; and
a control unit configured to control operations of the one or more sensor modules and the communication unit, and send measurement data including at least one of the sensor data and processed data obtained by processing the sensor data to the external device through the communication unit,
the measurement data including data indicating a direction of a stance of the golfer that is an angle formed by an axis connecting the first shoe and the second shoe and a cardinal direction, and
the external device includes:
a storage unit configured to store the sensor data;
a position measurement unit configured to specify position information indicating a shot position,
an analysis unit configured to, based on the measurement data, analyze the orientation of feet of the golfer when the golfer takes the shot; and
a screen generation unit configured to generate an analysis result screen that displays a result of analyzing the orientation of the feet of the golfer with the shot position by the analysis unit,
wherein the storage unit is configured to store the sensor data in association with the shot position, and
wherein the analysis result screen displays a map of all the holes of a golf course where the golfer is presently playing and the shot position with the direction of the stance on the map based on the analysis result.

2. The golf measurement system according to claim 1, wherein the one or more sensor modules include at least one sensor, as a sensor for measuring at least one of the orientation of the first shoe and the orientation of the second shoe, including one of:
an accelerometer attached to at least one of the first shoe and the second shoe;
a terrestrial magnetism sensor attached to at least one of the first shoe and the second shoe; and
a slope sensor attached to at least one of the first shoe and the second shoe.

3. The golf measurement system according to claim 2, wherein the one or more sensor modules include at least one sensor, as a sensor for measuring the positional relationship between the first shoe and the second shoe, including one of:
an ultrasonic sensor attached to at least one of the first shoe and the second shoe;
a radar sensor attached to at least one of the first shoe and the second shoe;
terrestrial magnetism sensors attached to both the first shoe and the second shoe;
atmospheric pressure sensors attached to both the first shoe and the second shoe;

accelerometers attached to both the first shoe and the second shoe; and slope sensors attached to both the first shoe and the second shoe.

4. The golf measurement system according to claim 2, wherein the external device further includes:
  an analysis unit configured to, based on the measurement data, analyze the orientation of feet of the golfer when the golfer takes the shot; and
  a display unit configured to display a result of the analyzing of the orientation of the feet of the golfer.

5. The golf measurement system according to claim 2, further comprising:
  a sensor unit-equipped golf club including a golf club to be used by the golfer and a sensor unit attached to the golf club,
  wherein the sensor unit includes one or more second sensor modules configured to measure second sensor data indicating a state of the golf club when the golfer takes the shot;
  a second communication unit connected to the external device wirelessly or over a wire; and
  a second control unit configured to control operations of the one or more second sensor modules and the second communication unit, and send second measurement data including at least one of the second sensor data and second processed data obtained by processing the second sensor data to the external device through the second communication unit.

6. The golf measurement system according to claim 2, wherein the external device is configured to identify a flight distance for the shot based on the position information of the shot focused on in the storage unit, and of another shot that follows the shot thereafter.

7. The golf measurement system according to claim 2, wherein the external device is configured to obtain information of the golf course where the golfer is presently playing including map information of the map of all holes of the golf course where the golfer is presently playing; and the screen generation unit is configured to generate an image in which an object indicating the shot position is superimposed on the map of the golf course where the golfer is presently playing and display the image in the analysis result screen.

8. The golf measurement system according to claim 1, wherein the one or more sensor modules include at least one sensor, as a sensor for measuring the positional relationship between the first shoe and the second shoe, including one of:
  an ultrasonic sensor attached to at least one of the first shoe and the second shoe;
  a radar sensor attached to at least one of the first shoe and the second shoe;
  terrestrial magnetism sensors attached to both the first shoe and the second shoe;
  atmospheric pressure sensors attached to both the first shoe and the second shoe;
  accelerometers attached to both the first shoe and the second shoe; and
  slope sensors attached to both the first shoe and the second shoe.

9. The golf measurement system according to claim 8, wherein the external device further includes:
  an analysis unit configured to, based on the measurement data, analyze the orientation of feet of the golfer when the golfer takes the shot; and
  a screen generation unit configured to generate an analysis result screen that displays a result of analyzing the orientation of the feet of the golfer with the shot position.

10. The golf measurement system according to claim 9, wherein the external device is configured to obtain information of a golf course where the golfer is presently playing including map information of all holes where the golfer is presently playing; and
  the screen generation unit is configured to generate an image in which an object indicating the shot position is superimposed on a map of the golf course where the golfer is presently playing and display the image in the analysis result screen.

11. The golf measurement system according to claim 8, wherein the external device further includes:
  an analysis unit configured to, based on the measurement data, analyze the orientation of feet of the golfer when the golfer takes the shot; and
  a display unit configured to display a result of the analyzing the of orientation of the feet of the golfer.

12. The golf measurement system according to claim 8, further comprising:
  a sensor unit-equipped golf club including a golf club to be used by the golfer and a sensor unit attached to the golf club,
  wherein the sensor unit includes one or more second sensor modules configured to measure second sensor data indicating a state of the golf club when the golfer takes the shot;
  a second communication unit connected to the external device wirelessly or over a wire; and
  a second control unit configured to control operations of the one or more second sensor modules and the second communication unit, and send second measurement data including at least one of the second sensor data and second processed data obtained by processing the second sensor data to the external device through the second communication unit.

13. The golf measurement system according to claim 8, wherein the external device is configured to identify a flight distance for the shot based on the position information of the shot focused on in the storage unit, and of another shot that follows the shot thereafter.

14. The golf measurement system according to claim 1, wherein the external device further includes:
  an analysis unit configured to, based on the measurement data, analyze the orientation of feet of the golfer when the golfer takes the shot; and
  a display unit configured to display a result of the analyzing of the orientation of the feet of the golfer.

15. The golf measurement system according to claim 1, further comprising:
  a sensor unit-equipped golf club including a golf club to be used by the golfer and a sensor unit attached to the golf club,
  wherein the sensor unit includes one or more second sensor modules configured to measure second sensor data indicating a state of the golf club when the golfer takes the shot;
  a second communication unit connected to the external device wirelessly or over a wire; and
  a second control unit configured to control operations of the one or more second sensor modules and the second communication unit, and send second measurement data including at least one of the second sensor data and second processed data obtained by processing the second sensor data to the external device through the second communication unit.

16. The golf measurement system according to claim 1, wherein the external device is configured to identify a flight distance for the shot based on the position information of the shot focused on in the storage unit, and of another shot that follows the shot thereafter.

17. The golf measurement system according to claim 1, wherein the external device is configured to obtain information of the golf course where the golfer is presently playing including map information of the map of all holes of the golf course where the golfer is presently playing; and the screen generation unit is configured to generate an image in which an object indicating the shot position is superimposed on the map of the golf course where the golfer is presently playing and display the image in the analysis result screen.

18. An ultrasonic or radar sensor device attachable to a first shoe and a second shoe of a pair of golf shoes to be worn by a golfer, the device comprising:
one or more sensor modules configured to measure sensor data pertaining to at least one of an orientation of the first shoe when the golfer takes a shot, an orientation of the second shoe when the golfer takes the shot, and a positional relationship between the first shoe and the second shoe when the golfer takes the shot;
a communication unit connected to an external device wirelessly or over a wire; and
a control unit configured to control operations of the one or more sensor modules and the communication unit, and send measurement data including at least one of the sensor data and processed data obtained by processing the sensor data to the external device through the communication unit,
wherein the control unit is configured to make the one or more sensor modules
a) measure the sensor data pertaining to at least one of the orientation of the first shoe and the orientation of the second shoe,
b) measure the sensor data pertaining to the distance between the first shoe and the second shoe, and
c) perform measurement a) and measurement b) at different times from each other,
wherein the one or more sensor modules include
a first ultrasonic or radar module attachable to the first shoe and transmitting ultrasonic or radar pulses to the second shoe and receiving ultrasonic or radar pulses from the second shoe, and
a second ultrasonic or radar module attachable to the second shoe and transmitting ultrasonic or radar pulses to the first shoe and receiving ultrasonic or radar pulses from the first shoe,
wherein measurements a) and b) measure the radar pulses for measuring shoe orientation and shoe distance at different times from each other or measurements a) and b) measure the ultrasonic pulses for measuring shoe orientation and shoe distance at different times from each other.

19. The ultrasonic or radar sensor device according to claim 18 in combination with sensor-device-equipped golf shoes, the combination comprising: the ultrasonic or radar sensor device; and the first shoe and the second shoe of the pair of golf shoes, wherein the ultrasonic or radar sensor device is attached to the first shoe and the second shoe.

20. A non-transitory computer readable medium storing a golf measurement program to be executed by a computer, the computer being connected to sensor module-equipped shoes, the sensor module-equipped shoes including a first shoe and a second shoe of a pair of golf shoes, and one or more sensor modules that are attached to the golf shoes and that are configured to measure sensor data pertaining to at least one of an orientation of the first shoe, an orientation of the second shoe, and a positional relationship between the first shoe and the second shoe, and the program causing the computer to:
obtain the sensor data from the one or more sensor modules;
analyze, based on the sensor data, the orientation of feet of a golfer when the golfer takes a shot including a direction of a stance of the golfer that is an angle formed by an axis connecting the first shoe and the second shoe and a cardinal direction;
specify position information indicating a shot position; and
generate an analysis result screen that displays a result of the analyzing of the orientation of the feet of the golfer with the shot position by the analyze operation,
wherein the analysis result screen displays a map of all the holes of a golf course where the golfer is presently playing and the shot position with the direction of the stance on the map based on the analysis result.

21. A non-transitory computer readable medium storing a golf measurement program to be executed by a computer, the computer being connected to an ultrasonic or radar sensor device attachable to a first shoe and a second shoe of a pair of golf shoes to be worn by a golfer, the ultrasonic or radar sensor device including a communication unit connected to an external device wirelessly or over a wire, and one or more ultrasonic or radar sensor modules configured to measure sensor data pertaining to at least one of an orientation of the first shoe when the golfer takes a shot and an orientation of the second shoe when the golfer takes a shot, and a distance between the first shoe and the second shoe when the golfer takes the shot, the program causing the computer to:
control operations of the one or more sensor modules and the communication unit;
send measurement data including at least one of the sensor data and processed data obtained by processing the sensor data to the external device through the communication unit; and
make the one or more ultrasonic or radar sensor modules
a) measure of the sensor data pertaining to at least one of the orientation of the first shoe and the orientation of the second shoe,
b) measure of the sensor data pertaining to the distance between the first shoe and the second shoe, and
c) perform measurement a) and measurement b) at different times from each other,
wherein the one or more sensor modules include
a first ultrasonic or radar module attachable to the first shoe and transmitting ultrasonic or radar pulses to the second shoe and receiving ultrasonic or radar pulses from the second shoe, and
a second ultrasonic or radar module attachable to the second shoe and transmitting ultrasonic or radar pulses to the first shoe and receiving ultrasonic or radar pulses from the first shoe,
wherein measurements a) and b) measure the radar pulses for measuring shoe orientation and shoe distance at different times from each other or measurements a) and b) measure the ultrasonic pulses for measuring shoe orientation and shoe distance at different times from each other.

22. Ultrasonic or radar sensor device-equipped golf shoes comprising:
- a first shoe and a second shoe of a pair of golf shoes to be worn by a golfer; and
- a sensor device attached to the golf shoes,
- wherein the sensor device includes:
  - an ultrasonic or radar transmitter attached to one of the first shoe and the second shoe and configured to emit ultrasonic or radar pulses, respectively; and
  - an ultrasonic or radar receiver attached to the one of the first shoe and the second shoe and configured to receive the ultrasonic or radar pulses, respectively, reflected from the other of the first shoe and the second shoe,
- wherein the distance between the first and second shoes is determined by a control unit based on the amount of time from the transmitting to the receiving of the ultrasonic or radar pulses.

23. A non-transitory computer readable medium storing a golf measurement program to be executed by a computer, the computer being connected to an ultrasonic or radar sensor device attached to a first shoe and a second shoe of a pair of golf shoes to be worn by a golfer, the ultrasonic or radar sensor device including an ultrasonic or radar pulse transmitter attached to one of the first shoe and the second shoe and configured to emit ultrasonic or radar pulses, respectively, and an ultrasonic or radar receiver attached to the one of the first shoe and the second shoe configured to receive the ultrasonic or radar pulses, respectively, reflected from the other of the first shoe and the second shoe, and the program causing the computer to:
- identify a relative direction of the first shoe to the second shoe based on the amount of time from the transmitting to the receiving of the ultrasonic or radar pulses.

* * * * *